(12) United States Patent
Lee et al.

(10) Patent No.: US 8,360,982 B2
(45) Date of Patent: Jan. 29, 2013

(54) METHOD AND APPARATUS FOR OPERATING A MICROMOTOR IN A FLUID USING A MOISTURE BARRIER

(75) Inventors: Warren Lee, Niskayuna, NY (US); Douglas Glenn Wildes, Ballston Lake, NY (US); Weston Blaine Griffin, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 716 days.

(21) Appl. No.: 12/315,747

(22) Filed: Dec. 5, 2008

(65) Prior Publication Data

US 2010/0145310 A1 Jun. 10, 2010

(51) Int. Cl.
*A61B 8/12* (2006.01)
*A61M 25/00* (2006.01)
(52) U.S. Cl. ...................................... 600/466
(58) Field of Classification Search ............... 600/437
See application file for complete search history.

(56) References Cited

U.S. PATENT DOCUMENTS

| | | | |
|---|---|---|---|
| 4,275,891 A | 6/1981 | Boes | |
| 4,375,818 A * | 3/1983 | Suwaki et al. | 600/463 |
| 4,561,110 A * | 12/1985 | Herbert | 604/408 |
| 5,456,256 A * | 10/1995 | Schneider et al. | 600/445 |
| 5,720,486 A | 2/1998 | Hutchings et al. | |
| 6,436,072 B1 * | 8/2002 | Kullas et al. | 604/151 |
| 6,733,457 B2 * | 5/2004 | Flesch et al. | 600/459 |
| 6,974,305 B2 * | 12/2005 | Garrett, III | 415/230 |
| 7,178,806 B1 | 2/2007 | Oitchko et al. | |
| 8,114,024 B2 * | 2/2012 | Solek et al. | 600/459 |
| 2003/0222407 A1 | 12/2003 | Hosokawa et al. | |
| 2004/0195778 A1 | 10/2004 | Smith et al. | |
| 2006/0043682 A1 | 3/2006 | Li et al. | |
| 2006/0192343 A1 | 8/2006 | Hashiba et al. | |
| 2008/0208230 A1 * | 8/2008 | Chin et al. | 606/167 |

* cited by examiner

*Primary Examiner* — Jacqueline Cheng
(74) *Attorney, Agent, or Firm* — Jason K. Klindtworth (57) ABSTRACT

A device and a method for sealing a micromotor with an optional associated gearbox are disclosed where, in one aspect of the present invention, a catheter tip comprises: a micromotor; an ultrasound imaging transducer; a gearbox mechanically coupled to the micromotor, the gearbox having a rotatable portion mechanically coupled to the ultrasound imaging transducer array; and a moisture barrier disposed so as to reduce or prevent acoustic coupling fluid from entering both the gearbox and the micromotor.

11 Claims, 6 Drawing Sheets

METHOD AND APPARATUS FOR OPERATING A MICROMOTOR IN A FLUID USING A MOISTURE BARRIER

BACKGROUND OF THE INVENTION

The subject matter disclosed herein relates to micromotor assemblies and, in particular, to micromotors with gearboxes operating in fluid environments.

The performance and reliability of a micromotor operating in a fluid environment can be adversely affected by the seepage of the fluid into the micromotor itself or into a gearbox attached to the micromotor. Fluid in the gearbox may substantially increase friction loading on the micromotor and correspondingly decrease the amount of torque available to drive an external load. Medical cardiac interventional procedures, such as real-time three-dimensional intra-cardiac echocardiography (4D ICE), for example, typically make use of a catheter-guided transducer array. The catheter also encloses a micromotor assembly for which it is desirable to avoid, or to mitigate, any additional functional loading resulting from the possible incursion of fluid into moving mechanical parts.

Figure 1:
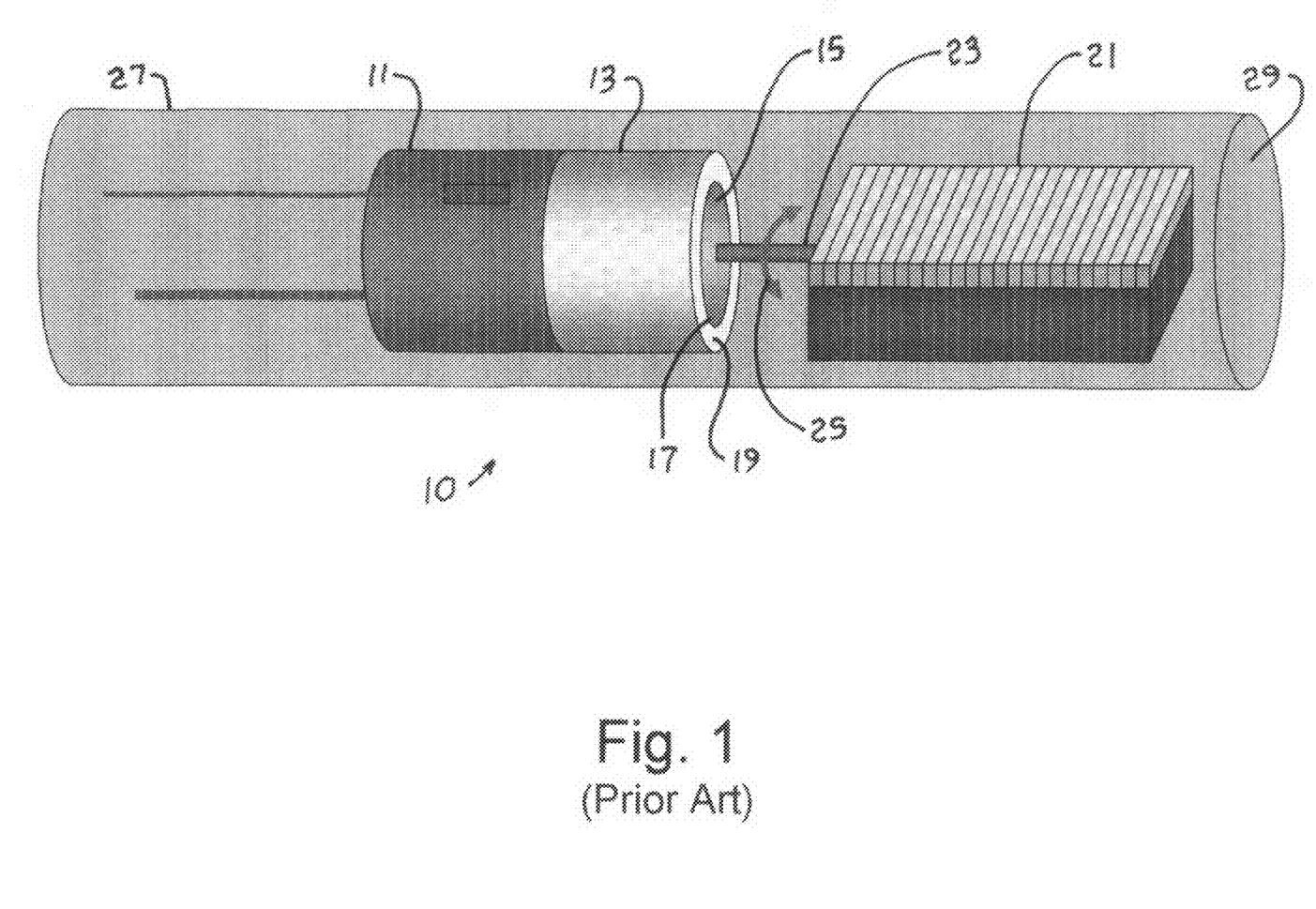
FIG. 1 shows an imaging catheter tip including a micromotor with associated gearbox attached to a one-dimensional array transducer, in accordance with the prior art.

FIG. 1 shows an imaging catheter tip 10 for use in a conventional cardiac interventional procedure, such as exemplified, for example, in commonly-assigned U.S. Patent Application Publication No. US 2008/0097403. The imaging catheter tip 10 includes a micromotor 11 with an associated gearbox 13 such that the micromotor 11 can impart an oscillating motion to an imaging transducer 21, the oscillation occurring about an axis of a drive shaft 23 as indicated by rotation arrow 25.

As the imaging transducer 21 is oscillated, a plurality of transducer elements in the imaging transducer 21 are electronically phased to form an electronic image by generating a three-dimensional dataset which may be sent to an associated data processing system (not shown). The micromotor 11, the gearbox 13, and the imaging transducer 21 are typically enclosed in a catheter housing 27 for insertion into a patient's body. The catheter housing 27 also typically encloses electrical conductors (not shown) for providing power to the micromotor 11 and the imaging transducer 21, and for sending signals from the imaging transducer 21 to the data processing system.

An acoustic coupling fluid 29 may be provided inside the catheter housing 27 as a medium for coupling ultrasound energy between the imaging transducer array 21 and a fluid medium (not shown) external to the imaging catheter tip 10. Accordingly, the micromotor 11, the gearbox 13, and the imaging transducer 21 are typically disposed within the acoustic coupling fluid 29. Under some circumstances, the acoustic coupling fluid 29 may, over time, leak or diffuse into either or both the gearbox 13 and the micromotor 11, resulting in additional friction loading in the gearbox 13. This leakage typically occurs through a cylindrical gap 17 formed between a rotating gearbox flange 15 and a non-rotating gearbox housing 19.

Because the operating range of the micromotor 11 may be limited by design constraints, operational torque needs to be efficiently outputted from the gearbox 13 to oscillate the imaging transducer 21. That is, it may not be feasible to increase the power output of the micromotor 11 so as to overcome the additional friction loading in the gearbox 13 resulting from the possible influx of ambient fluid. Moreover, simply increasing drive power to overcome higher gearbox loading may result in excessive heat buildup in the micromotor 11 and thus not conform to thermal regulations, such as may be set by regulatory agencies.

What is needed is an improved device and method for sealing a micromotor with an associated gearbox operating in a fluid environment.

BRIEF DESCRIPTION OF THE INVENTION

In one aspect of the present invention, a catheter tip is disclosed comprising: a micromotor; an ultrasound imaging transducer array; a gearbox mechanically coupled to the micromotor, the gearbox having a rotatable portion mechanically coupled to the ultrasound imaging transducer array; an acoustic coupling fluid; and a moisture barrier disposed so as to reduce or prevent the acoustic coupling fluid from entering the gearbox.

In another aspect of the present invention, a catheter tip is disclosed comprising: a micromotor; an ultrasound imaging transducer array; a gearbox mechanically coupled to the micromotor, the gearbox further having an output drive shaft rotatably coupled to the ultrasound imaging transducer array; an acoustic coupling fluid; and a membrane seal attached to the gearbox, the membrane seal having a resilient shaft opening enclosing the output drive shaft, the membrane seal functioning to reduce or prevent the acoustic coupling fluid from entering the gearbox.

In still another aspect of the present invention, a method is disclosed for reducing or preventing fluid from entering a gearbox mechanically coupled to a micromotor and to an ultrasound imaging transducer array. This method comprises: disposing a moisture barrier between the fluid and a cylindrical gap in the gearbox, the moisture barrier configured and positioned to allow the rotatable portion to rotate with respect to the micromotor, the cylindrical gap formed between a gearbox housing and a rotatable portion retained in the gearbox housing.

Other devices and/or methods according to the disclosed embodiments will become or are apparent to one with skill in the art upon review of the following drawings and detailed description. It is intended that all such additional devices and methods are within the scope of the present invention, and are protected by the accompanying claims.

DETAILED DESCRIPTION OF THE INVENTION

This invention describes methods to improve the performance and reliability of micromotors operating in fluid environments by preventing or mitigating the incursion of fluid into the motor or an associated gearbox, if provided. Disclosed are several embodiments of micromotor assemblies configured for protection from liquid incursion including: use of a fluid seal around the gearbox output, use of a flexible membrane surrounding the motor, use of a ferro-fluid seal around the output shaft, coating the gearbox with metal to slow the rate of diffusion, applying hydrophobic or hydrophilic material in order to control the location of the coupling fluid, and use of a labyrinth seal around the output shaft.

Figures 2, 3, 4:
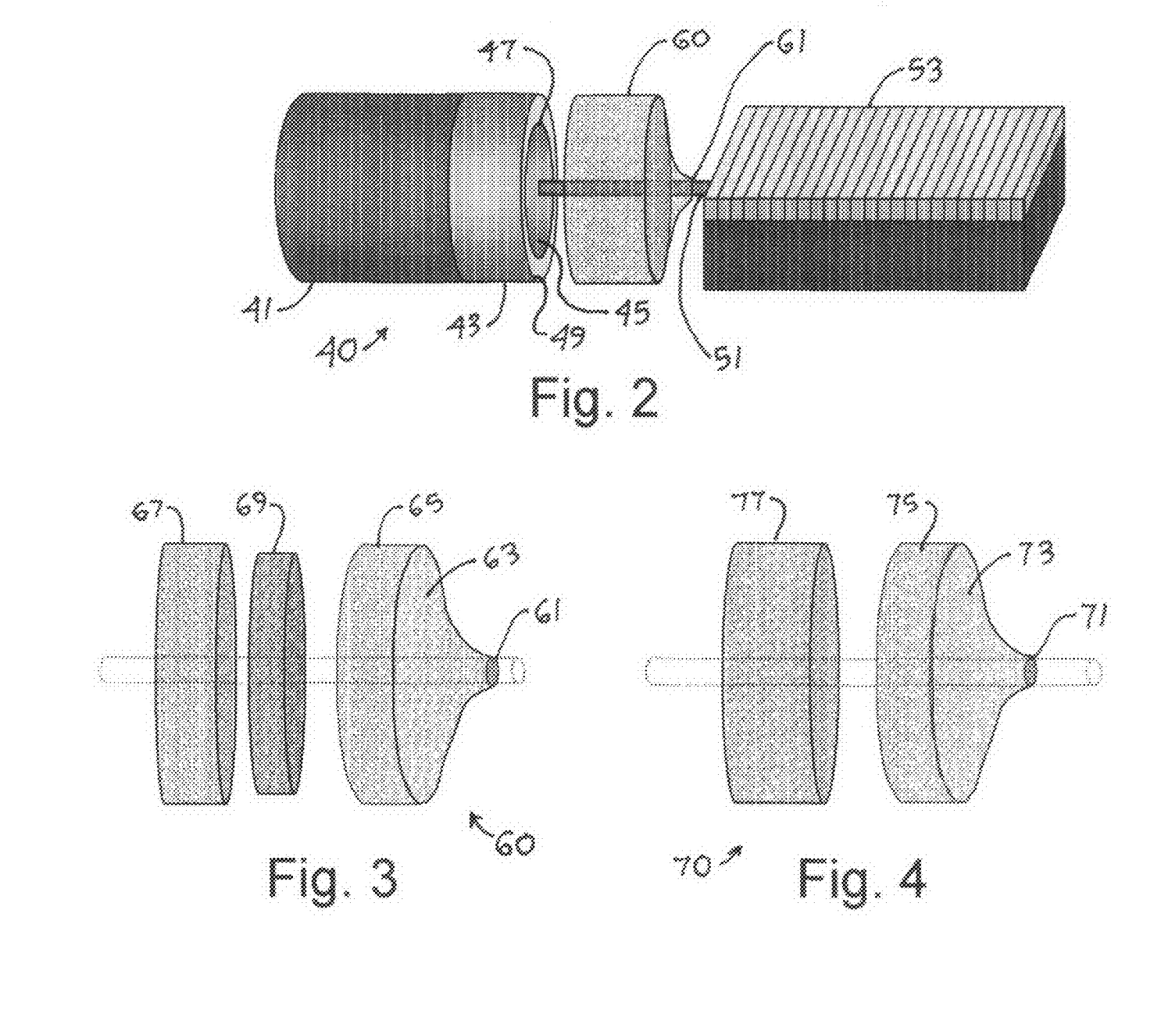
FIG. 2 shows an imaging catheter tip, in one aspect of the invention, including a micromotor and integral gearbox with a membrane seal attached about an output shaft.
FIG. 3 is an exploded view of the membrane seal of FIG. 2, showing attachment to the gearbox using an outer ring and an inner ring.
FIG. 4 is an exploded view of an alternate embodiment of the membrane seal of FIG. 2, showing attachment to the gearbox using an outer ring.

FIG. 2 shows a catheter tip 40, in one aspect of the present invention. The catheter tip 40 comprises a micromotor 41 mechanically coupled to a gearbox 43 which is, in turn, mechanically coupled to an ultrasound imaging transducer array 53. The micromotor 41 functions to oscillate the ultrasound imaging transducer array 53 via a rotatable portion such as an output drive shaft 51 coupled to an output drive flange 45 rotatably retained in a gearbox housing 49. As can be appreciated by one skilled in the art, the gearbox housing 49 may be optional and is shown for clarity of illustration. Accordingly, the innovative apparatuses and methods disclosed herein are likewise applicable to a catheter tip comprising only a micromotor 41. The catheter housing 27 and the acoustic coupling fluid 29, seen in FIG. 1, are not shown for clarity of illustration. Although the ultrasound imaging transducer array 53 is shown as a one-dimensional planar transducer array for purpose of illustration, it should be understood that an ultrasound transducer used in the catheter tip 40, or in any of the additional exemplary embodiments disclosed herein, is not limited to this configuration and may comprise any of: (i) a single transducer element, or (ii) a one-dimensional or two-dimensional, linear, sector, annular, convex, or curved ultrasound transducer array, as well known in the relevant art.

The catheter tip 40 includes a membrane seal 60 attached to the gearbox housing 49, such that the output drive shaft 51 extends through a resilient shaft opening 61 in the membrane seal 60. Preferably, the shaft opening 61 is in tension about the output drive shaft 51 so as to provide a barrier against the entry of the acoustic coupling fluid 29 into the membrane seal 60 at the output drive shaft 51. For clarity of illustration, the membrane seal 60 is here shown spaced apart from the gearbox housing 49. When attached to the gearbox housing 49, the membrane seal 60 serves as a moisture barrier between acoustic coupling fluid (not shown) and the interior of the gearbox 43. In particular, the membrane seal 60 is disposed so as to reduce or prevent the acoustic coupling fluid from leaking into the interior of the gearbox 43 via a circumferential gap 47 that may be present between the output drive flange 45 and the gearbox housing 49. Additionally, a fluid-repellent material (not shown) such as an oil, a gel, or a grease-like material, may be applied at the resilient opening 61 to provide lubrication and an additional barrier to moisture.

Figure 5:
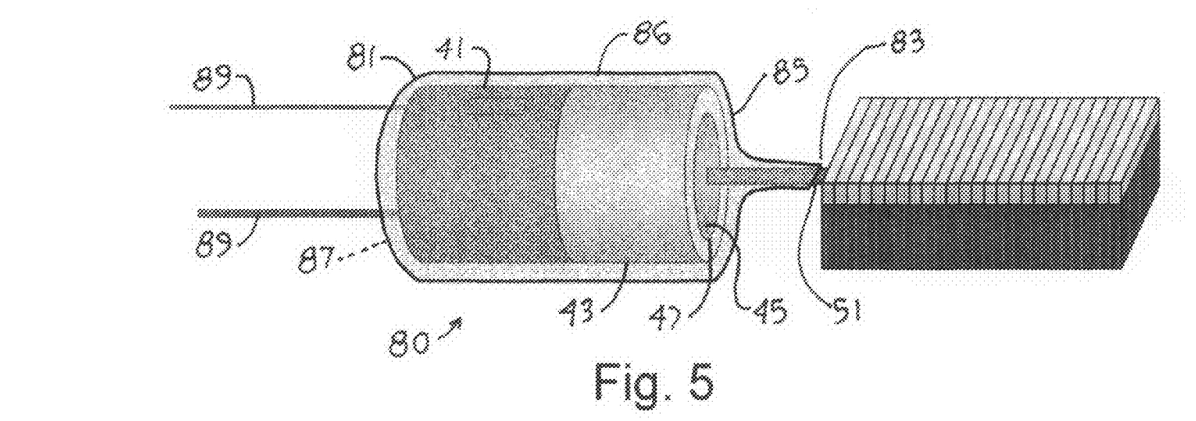
FIG. 5 shows an imaging catheter tip, in still another aspect of the invention, including a flexible membrane boot enclosing the micromotor and integral gearbox.

As best seen in FIG. 3, the membrane seal 60 may be fabricated from a substantially circular membrane 63 formed from an elastic material, such as silicone. The circular membrane 63 preferably has a generally cylindrical membrane rim 65 extending from the circumferential perimeter of the circular membrane 63. The resilient opening 61 is preferably located at or near the center of the circular membrane 63. The cylindrical membrane rim 65 may be retained between an outer membrane ring 67 and an inner membrane ring 69 to form the membrane seal 60. The outer membrane ring 67 and the inner membrane ring 69 may be formed from a metal such as stainless steel or nitinol. The outer membrane ring 67 may accordingly be attached to the gearbox housing 49, as indicated in FIG. 2, by a suitable method known in the art In an alternate exemplary embodiment, a membrane seal 70, shown in FIG. 4, may be fabricated from a substantially circular membrane 73 having a generally cylindrical membrane rim 75 extending from the circumferential perimeter of the circular membrane 73 and a resilient shaft opening 71 at or near the center of the circular membrane 73. The cylindrical membrane rim 75 may be bonded to an outer membrane ring 77, whereby the outer membrane ring 77 may be attached to the gearbox housing 49, as indicated in FIG. 2, by suitable means known in the art. For example, silicone material for the membrane 63 or the membrane 73 can be cast or molded in a "cap" shape, for subsequent attachment to respective cylindrical membrane rim 65 or 75, rather than fabricated from a flat sheet of silicone. The cap-shaped silicone could be formed directly onto the respective cylindrical membrane rim 65 or 75, or could be made as a separate part and then attached to the respective cylindrical membrane rim 65 or 75. This forming process would provide for desirable tension in the assembled membrane 63 or 73 about the respective cylindrical membrane rim 65 or 75. Such tension could also be provided by casting or molding the membrane 63 or 73 directly onto the respective cylindrical membrane rim 65 or 75 by using a membrane material composition with high cure shrinkage. It should be understood that, although the membrane seal 70 is shown in a circular configuration, the disclosed device is not limited to this configuration and that another geometric shape could be used so as to accommodate a particular micromotor and/or gearbox housing FIG. 5 shows a catheter tip 80, in another aspect of the present invention. The catheter tip 80 comprises a flexible membrane boot 81 shaped and sized to enclose the micromotor 41, the gearbox 43, and the output drive flange 45. The output drive shaft 51 extends through a resilient shaft opening 83 in a tapered membrane section 85 of the flexible membrane boot 81. In an exemplary embodiment, a cylindrical membrane section 86 of the flexible membrane boot 81 may be attached to the non-rotating micromotor 41 and the gearbox 43, and the tapered membrane section 85 may be attached to the rotating output drive shaft 51 at the resilient shaft opening 83. In an alternative exemplary embodiment (not shown), the tapered membrane section 85 may be attached directly to the ultrasound imaging transducer array 53.

The flexible membrane boot 81 is preferably configured to provide sufficient slack in the tapered membrane section 85 to allow the oscillating movement of the output drive shaft 51 without adversely loading the micromotor 41. In addition, suitable resilient openings (not shown) may be provided in a circular section 87 of the flexible membrane boot 81 for passage of electrical conductors 89 that provide power to the micromotor 41. Alternatively, the circular section 87 can be bonded to the electrical conductors 89. Accordingly, the flexible membrane boot 81 serves as a moisture barrier between fluid and the cylindrical gap 47.

Figure 6:
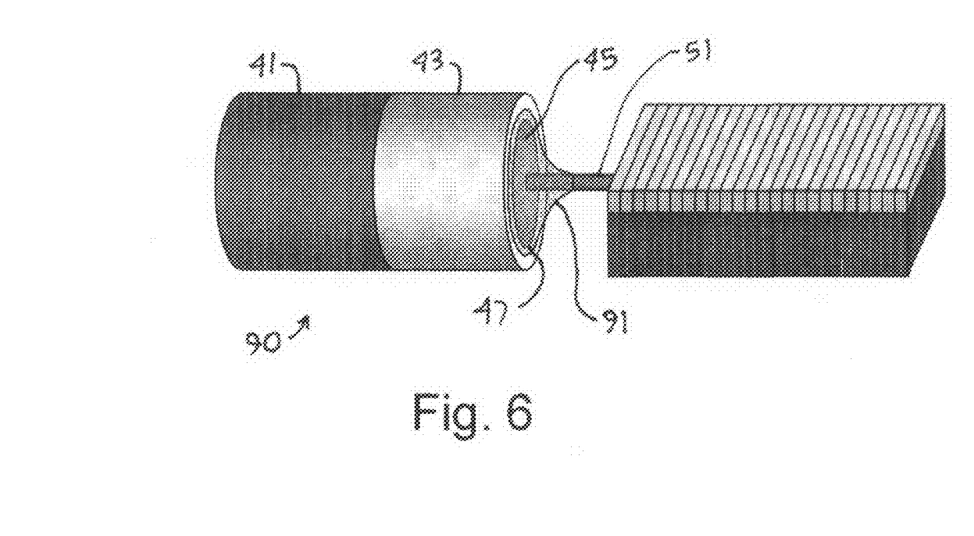
FIG. 6 shows an imaging catheter tip, in another aspect of the invention, having a fluid seal at the gearbox output.

FIG. 6 shows a catheter tip 90, in yet another aspect of the present invention. The catheter tip 90 comprises the micromotor 41, the gearbox 43, and a fluid seal 91 disposed to cover the rotatable flange 45. The fluid seal 91 further extends to also cover the cylindrical gap 47 and part of the output drive shaft 51. The fluid seal 91 preferably comprises a hydrophobic or hydrophilic material, such as a grease compound, that is resistant to dissolving in or being permeated by the ambient fluid.

Figure 7:
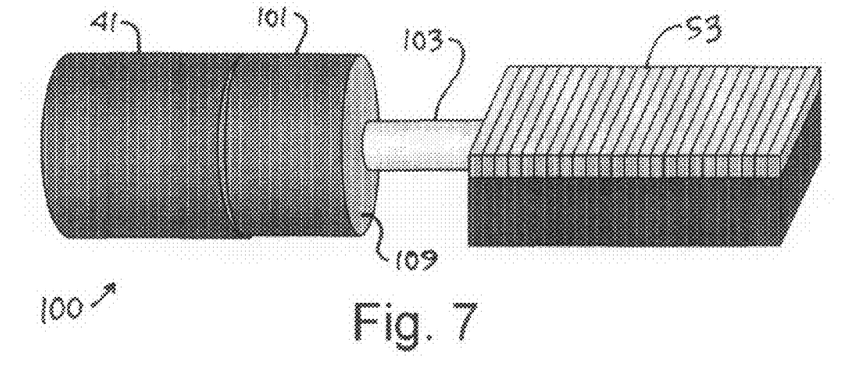
FIG. 7 shows an imaging catheter tip, in yet another aspect of the invention, including a micromotor and integral gearbox with a ferro-fluidic seal.

FIG. 7 shows a catheter tip 100, in still another aspect of the present invention. The catheter tip 100 comprises the micromotor 41, a gearbox 101 in mechanical communication with the micromotor 41, and an output drive shaft 103 extending from the gearbox 101 and in mechanical communication with the ultrasound imaging transducer array 53. The output drive shaft 103 is preferably formed from a ferromagnetic material. As shown in the cross-sectional view of FIG. 8, a ferro-fluid seal 105 is provided in the gearbox 101 such that the output drive shaft 103 passes through a shaft opening 107 in a circular face plate 109 of the ferro-fluid seal 105.

Figure 8:
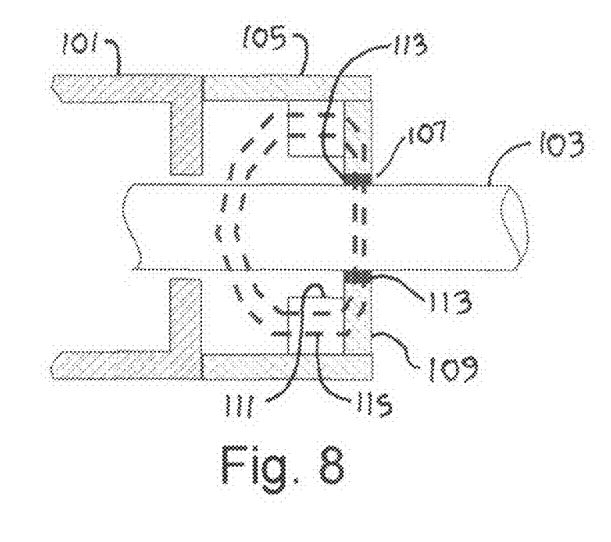
FIG. 8 is a cross-sectional view of the ferro-fluidic seal of FIG. 7 showing the ferro-fluidic seal retained in the gearbox at an output drive shaft.

The ferro-fluid seal 105 includes a non-rotating ring-magnet 111 affixed to the gear side of the circular face plate 109. The ring magnet 111 is magnetized such that the poles are aligned with the axis of the output drive shaft 103. The shaft opening 107 is sized and positioned in the circular face plate 109 so as to provide a tight tolerance fit with the output drive shaft 103. A ferro-fluid material forms an annular ferro-fluid sealant 113 disposed about the output drive shaft 103 in an annular gap present between the shaft opening 107 and the output drive shaft 103.

The circular face plate 109 functions to concentrate magnetic flux 115 across the annular gap, whereby the magnetic flux 115 serves to hold the annular ferro-fluid sealant 113 in the annular gap and, accordingly, about the output drive shaft 103 due to the concentration of the magnetic flux 115 across the annular gap. Preferably, the ferro-fluid material is not miscible with the ambient fluid (not shown), so as to assure retention of the ferro-fluid material in the annular gap. The ferro-fluid seal 105 thus functions to mitigate or prevent fluid from leaking past the output drive shaft 103 into the gearbox 101.

Figure 9:
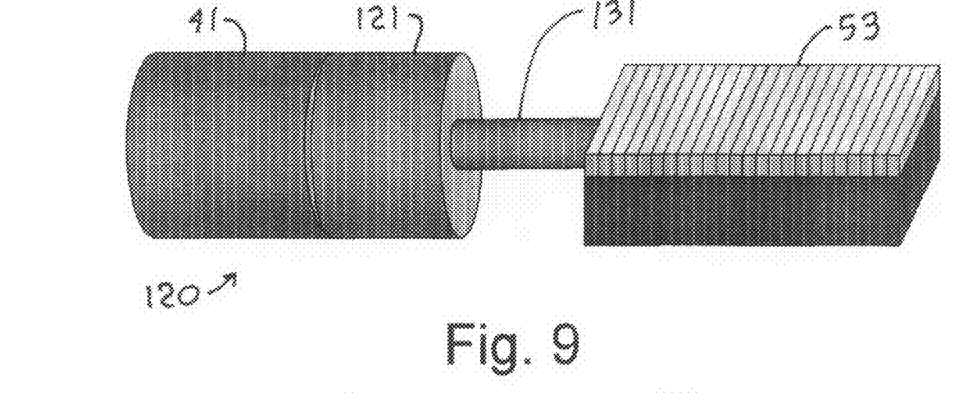
FIG. 9 shows an imaging catheter tip, in another aspect of the invention, including a micromotor and integral gearbox with a labyrinth seal.
Figure 10:
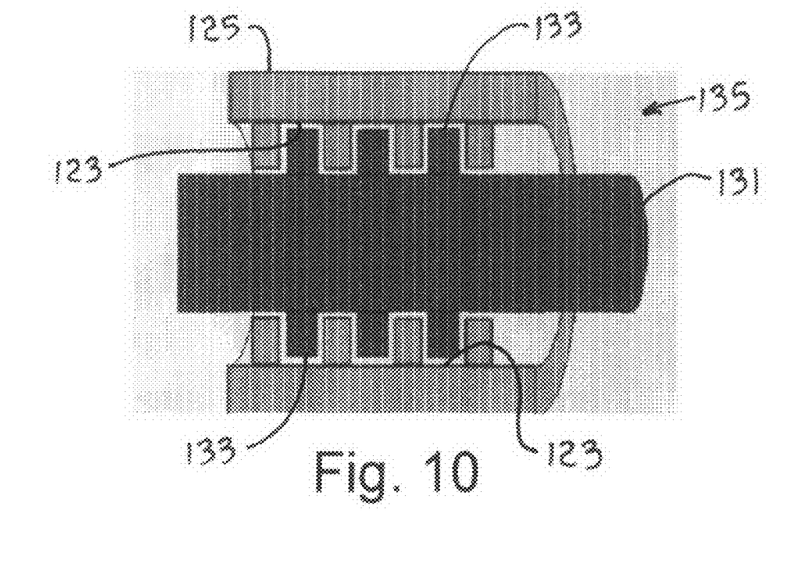
FIG. 10 is a cross-sectional view of the labyrinth seal of FIG. 9 showing an outer portion of the labyrinth seal disposed in the gearbox housing and a corresponding mating configuration of straight threads on a drive shaft.

FIG. 9 shows a catheter tip 120, in another aspect of the present invention. The catheter tip 120 comprises the micromotor 41, a gearbox 121 in mechanical communication with the micromotor 41, and an output drive shaft 131 in mechanical communication with the ultrasound imaging transducer array 53. As best seen in FIG. 10, a plurality of straight threads 133 are disposed on the output drive shaft 131, and a corresponding plurality of circumferential bore channels 123 are disposed in a gearbox housing 125 of the gearbox 121.

A labyrinth seal 135 is thereby formed by configuring each straight thread 133 to mate with a corresponding circumferential bore channel 123. The plurality of circumferential channels 123 comprise an outer non-rotatable portion of the labyrinth seal 135, and the plurality of straight threads 133 comprise an inner rotatable portion of the labyrinth seal 135. Any migration of fluid into the interior of the gearbox 121 must traverse a relatively long and convoluted path between the straight threads 133 and the circumferential bore channels 123. Accordingly, the labyrinth seal 135 functions as a moisture barrier to mitigate or prevent the leakage of fluid into the gearbox 121.

Figure 11:
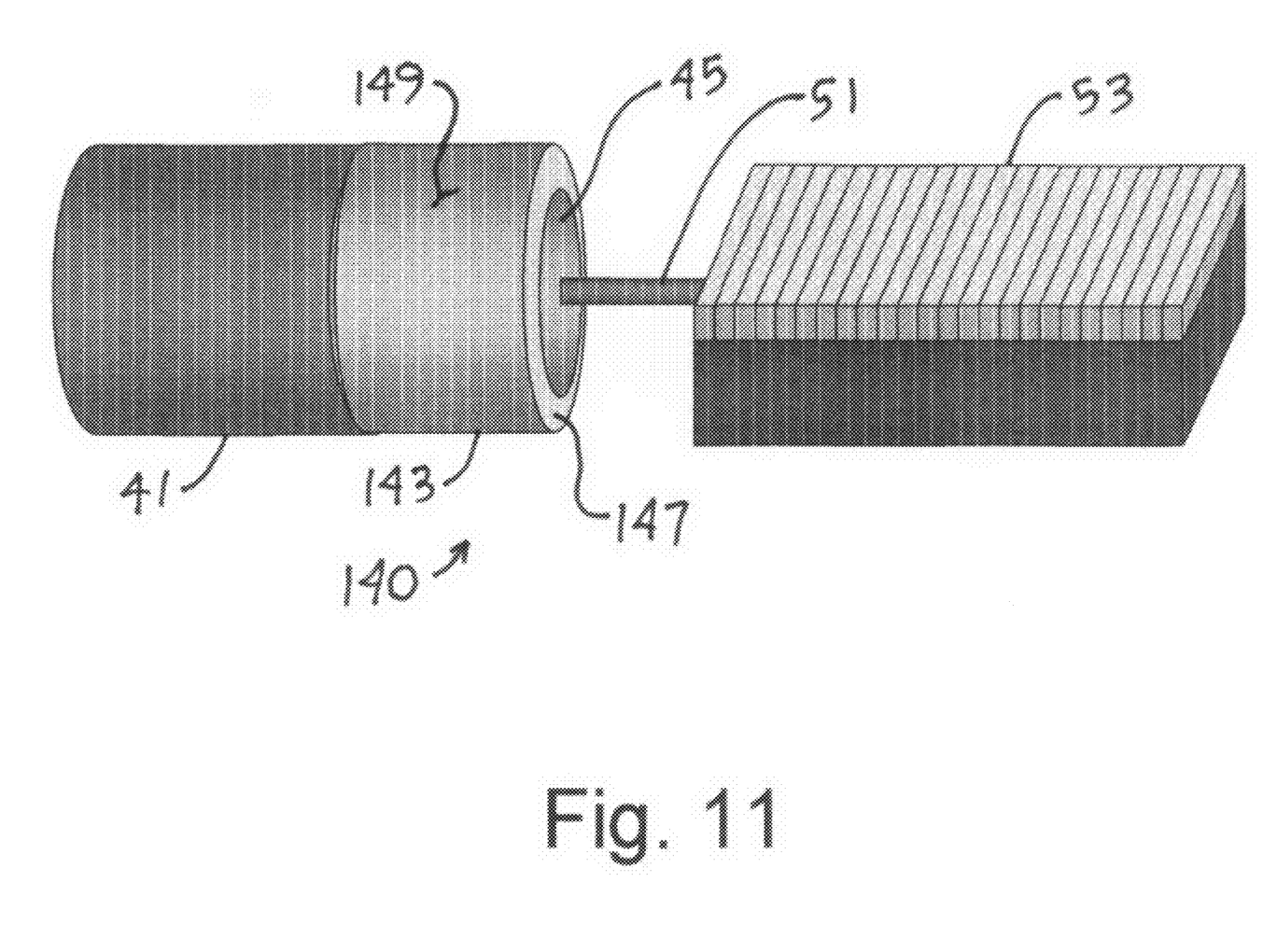
FIG. 11 shows an imaging catheter, in another aspect of the invention, including a micromotor with integral gearbox emplaced in a gearbox housing having a metal coating.

FIG. 11 shows a catheter tip 140, in another aspect of the present invention. The catheter tip 140 comprises the micromotor 41, a gearbox 143 in mechanical communication with the micromotor 41, the gearbox flange 45, and the output drive shaft 51 in mechanical communication with the ultrasound imaging transducer array 53. The gearbox 143 includes a gearbox housing 147 fabricated from a plastic material. The gearbox housing 147 includes a metal coating 149 to function as a moisture barrier and mitigate or prevent the leakage of fluid through the gearbox housing 147 into the gearbox 143. It can be appreciated that a similar metal coating can be applied to any of the gearbox housings in the various embodiments of the catheter tip assemblies disclosed above.

While the present invention is described with reference to various exemplary embodiments, it will be understood by those skilled in the art that various changes may be made and equivalence may be substituted for elements thereof without departing from the scope of the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. In particular, certain modifications may be made to the teachings of the invention to adapt to a particular situation without departing from the scope thereof. Therefore, it is intended that the invention not be limited to the embodiments disclosed above for carrying out this invention, but that the invention include all embodiments falling with the scope of the intended claims.

What is claimed is:

1. A catheter tip comprising:
    a micromotor disposed in an acoustic coupling fluid;
    an ultrasound imaging transducer rotatably coupled to said micromotor and disposed in the acoustic coupling fluid;
    a rotatable portion rotatably coupled to said ultrasound imaging transducer; and
    a moisture barrier comprised of one of a flexible membrane boot or a membrane seal including a resilient opening, the moisture barrier disposed so as to reduce or prevent the acoustic coupling fluid from entering said micromotor,
    wherein the membrane seal including the resilient opening is shaped and sized to attach to said micromotor and configured substantially circular and having a generally cylindrical membrane rim extending from a circumferential perimeter, the cylindrical membrane rim being retained by at least one membrane ring and wherein the membrane seal is configured to minimize rotational torque load on the micromotor and allow for rotational motion between the micromotor and the rotatable portion;
    wherein said flexible membrane boot is shaped and sized to enclose said micromotor and the rotatable portion and wherein said flexible membrane boot is configured to allow for rotational motion between the micromotor and the rotatable portion.

2. The catheter tip of claim 1, wherein said ultrasound imaging transducer comprises a device selected from the group consisting of: a single transducer element, a one-dimensional transducer array, a two-dimensional transducer array, a linear transducer array, a sector transducer array, an annular transducer array, a convex transducer array, or a curved transducer array.

3. The catheter tip of claim 1, further comprising a gearbox mechanically coupled to said micromotor and to said ultrasound imaging transducer.

4. The catheter tip of claim 3, wherein said gearbox comprises a the rotatable portion rotatably coupled to said ultrasound imaging transducer.

5. The catheter tip of claim 4, wherein said moisture barrier includes the membrane seal including the resilient opening, said membrane seal is attached to said gearbox, said resilient opening located so as to enable said rotatable portion to pass therethrough.

6. The catheter tip of claim 5 wherein said membrane seal further comprises at least one membrane ring attached to said membrane.

7. The catheter tip of claim 4, wherein said moisture barrier further comprises a hydrophobic or hydrophilic material disposed to cover at least said rotatable portion, said hydrophobic or hydrophilic material being resistant to dissolving in or being permeated by the ambient fluid.

8. The catheter tip of claim 3, wherein said moisture barrier further comprises a metal coating disposed on said gearbox.

9. A method for reducing or preventing an acoustic coupling fluid from entering a micromotor or a gearbox rotatably coupled to an ultrasound imaging transducer, said method comprising the step of:
   disposing said micromotor in the acoustic coupling fluid; and
   disposing a moisture barrier between the acoustic coupling fluid and at least one of said micromotor and said gearbox, said moisture barrier comprised of one of a flexible membrane boot or a membrane seal including a resilient opening, said moisture barrier configured and positioned to allow said ultrasound imaging transducer to rotate with respect to at least one of said micromotor and said gearbox,
   wherein the membrane seal including the resilient opening is shaped and sized to attach to said micromotor and configured substantially circular and having a generally cylindrical membrane rim extending from a circumferential perimeter, the cylindrical membrane rim being retained by at least one membrane ring and wherein the membrane seal is configured to minimize rotational torque on the micromotor and allow for rotational motion between the micromotor and the rotatable portion;
   wherein said flexible membrane boot is shaped and sized to enclose said micromotor and the rotatable portion and wherein said flexible membrane boot is configured to allow for rotational motion between the micromotor and the rotatable portion.

10. A catheter tip comprising:
a micromotor disposed in an acoustic coupling fluid;
an ultrasound imaging transducer disposed in said acoustic coupling fluid, said ultrasound imaging transducer attached to an output drive shaft rotatably coupled to said micromotor; and
a membrane seal having a resilient shaft opening enclosing said output drive shaft and configured substantially circular and having a generally cylindrical membrane rim extending from a circumferential perimeter, the cylindrical membrane rim being retained by at least one membrane ring, said membrane seal functioning to reduce or prevent said acoustic coupling fluid from entering said micromotor.

11. The A catheter tip comprising:
a micromotor disposed in an acoustic coupling fluid;
an ultrasound imaging transducer rotatably coupled to said micromotor and disposed in the acoustic coupling fluid; and
a moisture barrier comprised of a flexible membrane boot disposed so as to reduce or prevent the acoustic coupling fluid from entering said micromotor,
wherein said flexible membrane boot is shaped and sized to enclose said micromotor and a rotatable portion rotatably coupled to said ultrasound imaging transducer and includes a cylindrical membrane section attached to said micromotor and a tapered membrane section enclosing said rotatable portion.

* * * * *